United States Patent
Sullivan et al.

(10) Patent No.: US 9,107,885 B2
(45) Date of Patent: Aug. 18, 2015

(54) PRG4 TREATMENT FOR INTERSTITIAL CYSTITIS

(75) Inventors: Benjamin David Sullivan, San Diego, CA (US); Edward R. Truitt, III, San Diego, CA (US)

(73) Assignee: LUBRIS LLC, Framingham, MA (US)

( * ) Notice: Subject to any disclaimer, the term of this patent is extended or adjusted under 35 U.S.C. 154(b) by 205 days.

(21) Appl. No.: 13/390,084

(22) PCT Filed: Aug. 12, 2010

(86) PCT No.: PCT/US2010/045382
§ 371 (c)(1),
(2), (4) Date: Aug. 21, 2012

(87) PCT Pub. No.: WO2011/019963
PCT Pub. Date: Feb. 17, 2011

(65) Prior Publication Data
US 2012/0321693 A1 Dec. 20, 2012

Related U.S. Application Data

(60) Provisional application No. 61/233,810, filed on Aug. 13, 2009.

(51) Int. Cl.
*A61K 38/16* (2006.01)
*A61K 38/17* (2006.01)

(52) U.S. Cl.
CPC ................... *A61K 38/1709* (2013.01)

(58) Field of Classification Search
CPC .................................. A61K 38/1709
USPC ........................ 514/1.1, 18.7, 21.2
See application file for complete search history.

(56) References Cited

U.S. PATENT DOCUMENTS

| 2005/0220909 A1 | 10/2005 | Theoharides |
| 2005/0234013 A1* | 10/2005 | Parsons ........................ 514/54 |
| 2007/0275032 A1 | 11/2007 | Wimmer et al. |
| 2012/0052077 A1* | 3/2012 | Truitt et al. ................ 424/158.1 |

OTHER PUBLICATIONS

Hurst. A Deficit of Proteoglycans on the Bladder Uroepithelium in Interstitial Cystitis. European Urology Supplements.2:10-13, 2003.*
Bowie et al. Deciphering the Message in Protein Sequences: Tolerance to Amino Acid Substitutions. Science, 247:1306-1310, 1990.*
Whisstock et al. Prediction of proteinfunction from protein sequence and structure. Quarterly Reviews in Biophysics. 36(3):307-340, 2007.*
Lazar et al. Transforming Growth Factor αx: Mutation of Aspartic Acid 47 and Leucine 48 Results in Different Biological Activities. Molecular Cell Biology, 8:1247-1252, 1988.*
Reeck et al (1987) Cell, vol. 50, 667.*
Hurst et al. "A deficit of chondroitin sulfate proteoglycans on the bladder uroepithelium in interstitial cystitis" Urology. Nov. 1996;48(5):817-21.
Parsons et al. "Effect of pentosan polysulfate therapy on intravesical potassium sensitivity" Urology. Mar. 2002;59(3):329-33.
Schmidt et al. "Disulfide-bonded multimers of proteoglycan 4 PRG4 are present in normal synovial fluids" Biochim. Biophys. Acta. May 2009;1790(5):375-84. Epub Mar. 28, 2009.
Zhang et al. "Cartilaginous deposits in subchondral bone in regions of exposed bone in osteoarthritis of the human knee: histomorphometric study of PRG4 distribution in osteoarthritic cartilage" J. Orthop. Res. Jul. 2007;25(7):873-83.
International Search Report for PCT/US2010/045382, mailed May 2, 2011, 3 pages.
Written Opinion for PCT/US2010/045382, mailed May 2, 2011, 6 pages.
Supplemental European Search Report for EP 10808788.3, mailed Oct. 25, 2012, 7 pages.

* cited by examiner

*Primary Examiner* — Prema Mertz
(74) *Attorney, Agent, or Firm* — Thomas E. Jurgensen; Optima Law Group, APC

(57) ABSTRACT

The present invention relates to a disorder of the lower urinary tract, and in particular, reducing the symptoms (including treatment) of interstitial cystitis in vivo. In a preferred embodiment, the present invention relates to treatment formulations and methods for reducing interstitial cystitis in patients via administration of a therapeutically effective concentration of PRG4.

21 Claims, No Drawings

PRG4 TREATMENT FOR INTERSTITIAL CYSTITIS

CROSS-REFERENCE

This application is a 35 U.S.C. §371 U.S. National Stage application of International Patent Application No. PCT/US2010/20929, filed Aug. 12, 2010, and claims the benefit of U.S. Provisional Application No. 61/233,810, filed Aug. 13, 2009, which application is incorporated herein by reference.

FIELD OF THE INVENTION

The present invention relates to therapies designed to treat interstitial cystitis/painful bladder syndrome.

BACKGROUND

Interstitial cystitis (IC) is a chronic illness that strikes mainly the female sex, causing a change in the bladder walls such that a gradual loss of function of said organ results. The precise etiopathogenesis of the illness is still unknown and there are various postulated hypotheses. A first hypothesis is that a defect exists in the lining layers that make up the bladder mucosa. This mucosal layer is formed of so called GAGs (glycosaminoglycans), a layer of mucopolysaccharides with water repellent properties which line the internal wall of the bladder rendering it impermeable to urine. In pathological conditions, and for still partly unknown reasons, the walls become permeable due to a loss of GAGs hence allowing urine to penetrate into the bladder wall causing irritation and inflammation. This change can be apparent in different ways, from a slight thinning of the urothelium to actual ulcers (so called Hunners ulcers).

The symptoms appear to be those typical of a cystitis attack: frequency, urgency, incontinence, dysuria, burning and/or suprapubic pain, pelvic, perineal, vaginal and anorectal pain. Bacteria absence in the urine is frequent even though, as a result of acquired changes to the mucosa, cases are seen where germs superimpose onto the inflammation. This further complicates diagnosis and consequently confuses the case history.

The ailments can be present singly, or in more severe cases, simultaneously. Often associated with the functional discomfort (up to 60 micturitions over a day and night) is an intense pain unresponsive to common analgesic therapies which prevents the patient from being able to have a normal relationship and sex life.

SUMMARY OF THE INVENTION

The present invention relates to a disorder of the lower urinary tract, and in particular, reducing the symptoms (including treatment) of interstitial cystitis in vivo. In a preferred embodiment, the present invention relates to pharmaceutical compositions and therapeutic methods for reducing interstitial cystitis (including, e.g., reducing symptoms thereof) in patients.

In some embodiments, the present invention provides treatment compositions for reducing one or more of the following: urinary frequency, urinary urgency, and/or pelvic pain. In one embodiment, the present invention contemplates treating patients with interstitial cystitis (IC). In further embodiments, the present invention contemplates treating patients with radiation-induced cystitis, and bacterial cystitis or symptoms associated therewith. In further embodiments, the present invention contemplates treating patients with any one or more of the following: urinary frequency, urgency, and/or pelvic pain. In various embodiments, such therapies provide a method of treatment by administering any composition described herein.

In certain embodiments, provided herein is a method of treating IC, reducing urinary frequency, reducing urinary urgency, and/or reducing pelvic pain, said method(s) comprising supplying or replenishing PRG4 and other GAG's as provided herein to the bladder (e.g., to help to contribute to the return of homeostasis of the bladder wall). Moreover, because PRG4 spontaneously binds to tissue matrices, in some embodiments, the compositions and therapies described herein provide significantly improved residence time, as compared to alternative IC compositions and therapies based on high molecular weight polymers. In some instances, the ability to form spontaneous monolayers atop tissue surfaces reduces the concentration requirements of PRG4 to achieve therapeutic effect, which mitigates the viscosity limitations of other catheter-delivered therapies.

The present invention provides, in various embodiments, methods of treatment for interstitial cystitis (or symptoms associated therewith) in an individual, the method comprising administering to said individual (e.g., to the bladder or bladder mucosa thereof) a therapeutically effective amount of a concentration of PRG4 and/or a PRG4 inducer.

In one embodiment, said composition further comprises a heparinoid, or said treatment method further comprises administering a heparinoid to the individual. Any suitable haparin or heparinoid may be utilized, including a broad variety of heparins and related heparinoid compounds, such as, by way of non-limiting example: heparin sodium, pentosan polysulfate sodium, heparan sulfate, hyaluronic acid, chondroitin sulfate, glycosaminoglycans and the like. The present invention is not limited to any particular heparin.

In further or alternative embodiments, the composition further comprises a local anesthetic, or said treatment method further comprises administering a local anesthetic to the individual. In still further or alternative embodiments, the composition further comprises, or the method further comprises administering, a therapeutically effective concentration of phospholipids.

DETAILED DESCRIPTION OF THE INVENTION

Set forth in greater detail below are specific details related to novel compositions and methods for treatment and/or prevention of interstitial cystitis and/or related urinary tract conditions. In particular, the present invention provides specific teachings related to a superior pharmaceutical composition and related method for treatment and/or prevention of interstitial cystitis, by providing a composition suitable for direct bladder instillation that can be used as a treatment and/or preventative to alleviate or lessen at least one symptom of interstitial cystitis (IC) or a related urinary tract condition in man or in animals. In addition, the present invention provides compositions and surprisingly novel methods for the parenteral (systemic) and/or oral treatment and/or prevention of interstitial cystitis. The examples set forth herein are in no way intended to limit the scope of the invention. Those of skill in the art will realize that, given the teachings provided herein, many variations of the methods are possible that will fall within the scope of the of the invention.

The chronic and progressive development of interstitial cystitis and/or related urinary tract conditions justifies the need for a correct and prompt diagnosis, enabling the correct therapy to be initiated. Despite this considerations it has been calculated that with a patient affected by interstitial cystitis, about 5-7 years and an average of 4-5 specialists are required before the correct diagnosis is reached. As the causes of interstitial cystitis are unknown, the treatments are aimed solely at alleviating symptoms. The effectiveness of most treatments remains nevertheless low and symptoms often return after a brief period of improvement or momentary recovery.

Sodium hyaluronate, a molecule which is part of the GAG group, is currently used for therapeutic purposes in the form of a very dilute solution (about 0.08-0.5% by weight) applied through a catheter. As an example, there is a solution currently on the market (with 0.08% active principle by weight) comprising 40 mg of sodium hyaluronate (CYSTISTAT®) in suitable 50 ml dosage units which needs to be on maintained inside the bladder for as long as possible. Although the relatively low content of active principle is disadvantageous on the one hand for the purposes of therapy, this limitation derives on the other hand from the physico-chemical characteristics of hyaluronic acid whose aqueous solutions exhibit an overproportional increase in viscosity with concentration. Therefore, an indiscriminate increase in active principle concentration (despite its excellent solubility in water) is not feasible for the therapeutic purposes considered herein, because the consequent substantial viscosity increase would render application of the solution through a catheter difficult and increasingly painful. Consequently, in preparing therapeutic solutions it is not possible to make use of extended regions of the solubility range of hyaluronic acid; in order to intensify the known therapy, therefore, increasing the frequency of the full extent extended regions of applications of the dilute solutions remains the only option.

Treatments with dimethylsulfoxide (DMSO), approved for IC in 1977 on the basis of data from uncontrolled trials, can be useful with weekly intravesical instillations for 6 to 8 weeks then every two weeks for 3-12 months for maintenance. However DMSO therapy results in benefit for approximately 50% of IC patients treated and the treatment takes a long time to reduce symptoms. Furthermore, this therapy causes pain that is unrelieved by local anesthetics by themselves due to their lack of absorption into the bladder wall. Narcotics are given for immediate relief of symptoms however they are only minimally effective. Some patients benefit from formal 8- to 12-week, one-on-one course of behavior modification. Patients are also advised to avoid potassium-rich foods, particularly citrus fruits, tomatoes, chocolate, and coffee.

Therefore, treatments that would both benefit a larger portion of the patient population, provide immediate relief of symptoms without causing additional pain, without requiring extensive alterations in diet, and further provide reversal of the disease process over time are necessary. The present invention meets that challenge by providing compositions, detection methods and novel IC management treatment methods with the benefits described herein.

In one embodiment, the invention provides a composition suitable for direct instillation into the bladder that is useful for the treatment and/or prevention of interstitial cystitis, the composition comprising therapeutic amount of PRG4. In particular embodiments, the compositions described herein comprise PRG4 in a concentration suitable for providing a therapeutically effective amount of PRG4 to the desired location and being suitable for delivery of the PRG4 to the desired location (e.g., directly to the bladder).

In certain embodiments, any suitable concentration of PRG4 is optionally utilized in the methods and compositions described herein. In specific embodiments, the pharmaceutically effective concentration of PRG4 is in a range of 10-10,000 μg/mL, preferably 50-5,000 μg/mL, and more preferably 100-300 μg/mL.

In certain embodiments, a composition described herein further comprises, or a method described herein further comprises administering to individual (e.g., man or animal), a heparinoid. Any suitable heparinoid is optionally utilized. Indeed a variety of heparins and related heparinoid compounds are contemplated, including, but not limited to one or more of the following: heparin sodium, pentosan polysulfate sodium, heparan sulfate, glycosaminoglycans and the like. The present invention is not limited to any particular heparin.

In one embodiment, said composition comprises, or said method comprises administering, at least 10 units, at least 100 units, at least 1,000 units, at least 5,000 units, or at least 10,000 units ("USP Unit") of heparin per unit dose. In one embodiment, said composition comprises, or said method comprises administering, at least 10,000 units of heparin per unit dose. In one embodiment, said composition comprises, or said method comprises administering, from 10,000 to 40,000 units of heparin per unit dose. Accordingly in some embodiments, said composition comprises, or said method comprises administering, 100 units, 10,000 units, 40,000 units (or any amount between 100 units and 40,000 units) of heparin per unit dose. In one embodiment, said composition comprises, or said method comprises administering, from 100 mg to 600 mg pentosan polysulfate sodium per unit dose. Accordingly in some embodiments, said composition comprises, or said method comprises administering, 100 mg, 200 mg, 300 mg, 400 mg, 500 mg, 600 mg (or any amount between 100 mg and 600 mg) pentosan polysulfate sodium per unit dose. Heparinoids may be utilized in various embodiments herein and may be utilized in any suitable amount, such as those described above. Moreover, other heparinoids may also be utilized, and utilized in quantities chosen according to their activity and therapeutic benefit in a method described herein.

In various embodiments, heparin utilized in the methods and/or composition described herein is in any suitable form. In some embodiments, the heparin is or comprises high molecular weight heparin, low molecular weight heparin, or a combination thereof. In some embodiments, heparin is a higher molecular weight species ranging from 8,000-40,000 daltons. In some embodiments, heparin is lower molecular-weight heparin, having a molecular weight ranging from 2,000-8,000 daltons (e.g., pentosan polysulfate sodium ranging from 4,000-6,000 daltons). HMW and LMW heparins utilized herein may be prepared or procured in any suitable manner. In some embodiments, LMW heparins are made by enzymatic or chemical controlled hydrolysis of unfractionated heparin and have very similar chemical structure as unfractionated heparin except for some changes that may have been introduced due to the enzymatic or chemical treatment.

In one embodiment, heparin or another heparinoid is a heparin salt, e.g., a pharmaceutically acceptable salt (e.g. heparin sodium, pentosan polysulfate sodium, heparan sulfate). As used herein, the phrases "pharmaceutically acceptable salts", "a pharmaceutically acceptable salt thereof" or "pharmaceutically accepted complex" for the purposes of this application are equivalent and refer to derivatives prepared from pharmaceutically acceptable non-toxic acids or bases including inorganic acids and bases and organic acids and bases. Since the compound of the present invention is acidic, salts may be prepared from pharmaceutically acceptable non-toxic bases. A suitable pharmaceutically acceptable counterion for the heparin is a positively-charged counterion such as sodium, calcium, ammonium, and substituted ammonium.

In some embodiments, the amount of the heparinoid in the compositions of the invention will vary depending on the subject, severity and course of the disease, the subject's health and response to treatment and the judgment of the treating physician. Accordingly, in some instances, the dosages of the molecules should be titrated to the individual subject. In certain embodiments, a method described herein further comprises titrating the amount of composition, and/or amount of PRG4, heparinoid, or the like administered to an individual (e.g., based on the individual's response to therapy).

As discussed above, various USP heparin unit doses may be utilized in the compositions and methods described herein. For example, in one embodiment, heparin contains at least 130 USP units per mg. As used herein, "USP" unit refers to the quantity of heparin that prevents 1.0 ml of citrated sheep plasma from clotting for 1 hour after the addition of 0.2 ml of 1% $CaCl_2$ at 20 degree C. when compared to a USP reference standard (defined as units/ml). As used herein, "IU" refers to the quantity of heparin that is active in assays as established by the Fifth International standard for Unfractionated Heparin (WHO-5) (defined as International Units/ml) (Linhardt, R. J. & Gunay, N. S. (1999) Semin Thromb Hemost 25, 5-16.).

In a further exemplary embodiment, Pentosan polysulfate sodium (PPS) may be given at a dose of 300 mg per day, although a higher dose may be necessary to obtain a successful result in some cases. For example, for men with IC, PPS may be prescribed at about 600 mg per day, in two or three divided doses.

In accordance with the practice of the invention, merely by way of example, when the heparinoid is heparin, the amount of heparinoid in the composition may be any suitable amount, e.g., between about 0.5 mg to about 1000 mg of heparin per unit dose (for example about 500 units of heparin to about a maximum of 100,000 units of heparin (e.g., about 1000 USP units to about 100,000 USP units per dose or 100 USP units to about 600 USP units per unit dose of heparin)).

In accordance with the practice of the invention, merely by way of example, when the heparinoid is pentosan polysulfate sodium, the amount of heparinoid in the composition may be about 1 mg to about 600 mg of pentosan polysulfate sodium per unit dose (for example about 100 mg to about 600 mg per unit dose of pentosan polysulfate sodium).

In accordance with the practice of the invention, merely by way of example, when the heparinoid is heparan sulfate, the amount of heparinoid in the composition may be about 0.5 mg to about 10,000 mg of heparan sulfate per unit dose (for example about 100 mg to about 300 mg per unit dose of heparan sulfate).

In accordance with the practice of the invention, merely by way of example, when the heparinoid is hyaluronic acid, the amount of heparinoid in the composition may be about 1 mg to about 600 mg of hyaluronic acid per unit dose (for example about 10 mg to about 100 mg per unit dose of hyaluronic acid).

In accordance with the practice of the invention, merely by way of example, when the heparinoid is chondroitin sulfate, the amount of heparinoid in the composition may be about 1 mg to about 10,000 mg of chondroitin sulfate per unit dose (for example about 100 mg to about 300 mg per unit dose of chondroitin sulfate).

In accordance with the practice of the invention, merely by way of example, when the heparinoid is heparin sodium, the amount of heparinoid in the composition may be about 10 mg to about 600 mg of heparin sodium per unit dose.

In certain embodiments, the composition further comprises, or the method further comprises administering, a local anesthetic. The anesthetic (e.g., the local anesthetic) in the compositions of the invention includes but is not limited to any of benzocaine, lidocaine, tetracaine, bupivacaine, cocaine, etidocaine, flecamide, mepivacaine, pramoxine, prilocalne, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof, or a combination thereof. Preferably, the anesthetic (e.g., local anesthetic) is selected from the group consisting of lidocaine, bupivicaine, benzocaine, tetracaine, etidocaine, flecamide, prilocalne, and dibucaine, or a combination thereof. In a preferred embodiment, the local anesthetic comprises at least one of lidocaine, bupivacaine, and mepivacaine. Most preferably, the local anesthetic is lidocaine. Anesthetics described herein may be utilized in any suitable manner. In some instances, amount of the anesthetic in the compositions or method may vary or may be adjusted depending on the subject, severity and course of the disease, the subject's health and response to treatment and the judgment of the treating physician. Accordingly, in some embodiments, dosages of the molecules are optionally titrated to the individual subject. Further, in certain instances, the local anesthetic is provided in amounts and concentrations suitable for providing local anesthetic relief. For example, the amount of anesthetic agent in the compositions may be in the range of about 1 mg to about 1 g, about 5 mg to about 600 mg, about 10 mg to about 400 mg, about 50 mg to about 250 mg, or the like per unit dose. Generally, any suitable concentration of local anesthetic may be utilized, such as, by way of non-limiting example, about 0.01 wt. % to about 20 wt. %, or more. In more specific embodiments<a suitable concentration of anesthetic includes, e.g., 0.05 wt. % to 10 wt. %, 0.1 wt. % to 5 wt %, 0.5 wt. % to 3 wt. %, or the like. In one exemplary embodiment, the amount of lidocaine can be 10 mL of 1% lidocaine per unit dose or 16 mL of 2% lidocaine per unit dose.

In certain embodiments, the invention further comprises phospholipids. Exemplary phospholipids include, but is not limited to, L-a-dipalmitoylphosphatidylcholine, phosphatidylcholine, phosphatidylethanolamine and sphingomyelin.

In certain embodiments, the invention further or alternatively (i.e., alternatively to PRG4) comprises a PRG4 inducer. The PRG4 inducing compounds encompassed in the present invention include, but are not limited to, an androgen, an androgen analogue, a selective androgen receptor modulator, a selective estrogen receptor modulator, an estrogen antagonist, an aromatase inhibitor, an antiprotease, a proinflammatory cytokine antagonist, a cytokine release inhibitor, an antiinflammatory cytokine, an antiinflammatory agent, a NF-k-B inhibitor, and a proteasome inhibitor.

In certain embodiments, the androgen analogues include, but are not limited to 17a-methyl-17b-hydroxy-2-oxa-5a-androstan-3-one derivative, a nitrogen-substituted androgen, a testosterone derivative, a 4,5a-dihydrotestosterone derivative, a 19-nortestosterone derivative, a 17b-hydroxy-5a-androstane derivative containing a ring A unsaturation, or a structural subclass of androgens comprising androgenic compounds with unusual structural features.

In certain embodiments, the selective androgen receptor modulators (SARMs) include, but are not limited to, arylpropionamide compound, such as S-3-(4-acetylamino-phenoxy)-2-hydroxy-2-methyl-N-(4-nitro-3-trifluoromethylphenyl)-propionamide [S-4], or S-3-(4-fluorophenoxy)-2-hydroxy-2-methyl-N-(4-nitro-3-trifluoromethyl-phenyl)-propionamide [S-1]), bicyclic hydantoin, quinoline, tetrahydroquinoline, and analogues thereof, that have in vivo androgenic and anabolic activity of a non-steroidal ligand for the androgen receptor.

In certain embodiments, the selective estrogen receptor modulators (SERMs) include, but are not limited to, non-steroidal ligands of the estrogen receptor that are capable of inducing a number of conformational changes in the receptor and thereby eliciting a variety of distinct biological profiles (e.g. prevention of estrogen-induced inflammation), and estrogen antagonists (steroidal, non-steroidal) regardless of receptor affinity. In certain embodiments, the PRG4 inducing compounds also include aromatase inhibitors, antiproteases, pro-inflammatory cytokine antagonists, such as an anti-TNFα antibody, a soluble TNFa receptor, or an IL-1 receptor antagonist, cytokine release inhibitors, NF-k-B inhibitors, cytokines (e.g. TGF-b) anti-inflammatory agents, such as cyclosporine A, omega 3 and 6 fatty acids, or proteasome inhibitors.

In some embodiments, the present invention provides pharmaceutical compositions and methods for reducing one or more of the following: urinary frequency, urinary urgency, and/or pelvic pain. In one embodiment, the present invention contemplates treating patients with interstitial cystitis (IC). In further embodiments, the present invention contemplates treating patients with radiation-induced cystitis, and bacterial cystitis or symptoms associated therewith. In further embodiments, the present invention contemplates treating patients with any one or more of the following: urinary frequency, urinary urgency, and/or pelvic pain. In some embodiments, such compositions comprise or such therapies include administering a therapeutically effective amount of PRG4, PRG4 inducer, or any composition comprising PRG4 or PRG4 inducer described herein.

In certain embodiments, the pharmaceutical composition further comprises or method further comprises administering a local anesthetic. The present invention is not limited to any particular local anesthetic or formulation. In some embodiments, the local anesthetic comprises lidocaine. Typically, the local anesthetic is selected from the group consisting of benzocaine, lidocaine, tetracaine, bupivacaine, cocaine, etidocaine, flecamide, mepivacaine, pramoxine, prilocalne, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Preferably, the local anesthetic is selected from the group consisting of lidocaine, bupivicaine, benzocaine, tetracaine, etidocaine, flecamide, prilocalne, and dibucaine. More preferably, the local anesthetic is lidocaine.

In certain embodiments, a PRG4 or PRG4 inducer containing composition described herein is formulated in any manner suitable for physiological administration. In some embodiments, such compositions comprise PRG4 (and/or PRG4 inducer) and a pharmaceutically acceptable carrier (e.g., a carrier suitable for delivery of the active to the urothelium, bladder, or bladder mucosa). In some embodiments, the carrier is a pharmaceutically acceptable liquid or solid. In specific embodiments the active ingredients are suspended in pharmaceutically acceptable buffer (e.g., at a physiologically acceptable pH). Any suitable buffering compounds maybe utilized in such compositions. For example, the buffering compounds in the compositions of the invention includes but is not limited to bicarbonate buffer, THAM or Tris (Tris (hydroxymethyl)aminomethane) buffer, MOPS buffer (3-(N-morpholino)propanesulfonic acid), HEPES (N-(2-hydroxyethyl)piperazine-N-(2-ethanesulfonic acid) buffer, ACES (2-[(2-amino-2-oxoethyl)amino]ethanoesulfonic acid) buffer, ADA (N-(2-acetamido)-2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid) buffer, CHES (2-(N-cyclohexylamino)ethanesulfonic acid) buffer, DIPSO (3-[N,N-bis(2-hydroxyethyl)amino]-2-hydroxy-propanesulfonic acid) buffer, HEPPS(N-(2-hydroxyethylpiperazine)-N'-(3-prop anesulfonic acid) buffer, HEPPSO(N-(2-hydroxyethyl)piperazine-N'-(2-hydroxypropanesulfonic acid) buffer, MES (2-(N-morpholino)ethanesulfonic acid) buffer, triethanolamine buffer, imidazole buffer, glycine buffer, ethanolamine buffer, phosphate buffer, MOPSO (3-(N-morpholino)-2-hydroxypropanesulfonic acid) buffer, PIPES (piperazine-N,N'-bis(2-ethanesulfonic acid) buffer, POPSO (piperazine-N,N'-bis(2-hydroxypropaneulfonic acid) buffer, TAPS(N-tris[hydroxymethyl]methyl-3-aminopropanesulfonic acid) buffer; TAPSO (3-[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, and 2-amino-2-methyl-1-propanol buffer. In a preferred embodiment, the buffer is sodium bicarbonate buffer, Tris buffer, phosphate buffer, MOPS buffer, and HEPES buffer, or a combination thereof. In a preferred embodiment, the buffering compound comprises at least one of sodium bicarbonate and THAM (tromethamine or Tris hydroxymethylpropyl). More preferably, the buffering compound is sodium bicarbonate. The amount of the buffering compound in the compositions of the invention will vary depending on the subject, severity and course of the disease, the subject's health and response to treatment and the judgment of the treating physician. Accordingly, the dosages of the molecules should be titrated to the individual subject. For example, the amount of the buffering compound(s) in the compositions of the invention is the amount sufficient to raise the pH of the composition to above about pH 7; preferably above pH 8; or in a range between about pH 7-12. For example, the amount of sodium bicarbonate may be about 3 mL of 8.4% sodium bicarbonate (w/v) per unit dose. In certain embodiments, the present invention further comprise an osmolar component that provides an isotonic or nearly isotonic solution compatible with human cells and blood. Typically the osmolar component is a salt, such as sodium chloride, or a sugar or a combination of two or more of these components. The sugar may be a monosaccharide such as dextrose, a disaccharide such as sucrose or lactose, a polysaccharide such as dextran 40, dextran 60, or starch, or a sugar alcohol such as mannitol. All components of the composition contribute to the osmolarity of the solution but to achieve an isotonic or near-isotonic solution, the contributions of these components should be taken into account to ensure that the proper osmolar component is added and not added in excess which would result in a hypertonic solution.

In some embodiments, individuals treated according to the methods described herein or with the compositions described herein may suffer from inflamed urothelium and/or bladder. Therefore, in some instances, due to the inflamed, permeable nature of the urothelium, a preferred solution or liquid carrier is isotonic or near isotonic. Hypotonic solutions are known to result in cell lysis, particularly of red blood cells, but other cells may also be damaged leading to increased cell damage in the bladder and accessible underlying layers. Hypertonic solutions may result in cell shrinkage which may enlarge pores or weaken cell junctions allowing urinary solutes more access to underlying cell layers leading to further damage, pain and inflammation. The addition of an osmolar component to the composition to form an isotonic or near isotonic solution ensures that neither of these two possibilities occurs. The osmolar component is optionally utilized in any suitable amount. For example, in one embodiment, the osmolar component is 0.9% sodium chloride, or somewhat less as the other components in the solution also contribute to the solution's osmolarity and thus should be taken into account. In some embodiments, the osmolar component is a salt, such as sodium chloride, or a sugar or a combination of two or more of these components. The sugar may be a monosaccharide such as dextrose, a disaccharide such as sucrose or lactose, a polysaccharide such as dextran 40, dextran 60, or starch, or a sugar alcohol such as mannitol. All components of the composition contribute to the osmolarity of the solution but to achieve an isotonic or near-isotonic solution, the contributions of these components should be taken into account to ensure that the proper osmolar component is added and not added in excess which would result in a hypertonic solution.

The osmolar component of the compositions of the invention includes but is not limited to sodium chloride, dextrose, dextran 40, dextran 60, starch and mannitol, or a combination thereof.

The amount of the osmolar component in the compositions of the invention will vary depending on the subject, severity and course of the disease, the subject's health and response to treatment and the judgment of the treating physician. Accordingly, the dosages of the molecules should be titrated to the individual subject. For example, the amount of the osmolar component(s) in the compositions of the invention is at least 50 milliosmoles.

Additional embodiments of the invention include pharmaceutical compositions comprising the composition of the invention and a pharmaceutically acceptable carrier.

Examples of suitable pharmaceutical carriers and adjuvants include any material which when combined with the components of the compositions of the invention retain the component's activity, and is non-reactive with the subject's immune system. These carriers and adjuvants include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g. oil/water emulsion), salts or electrolytes such as, disodium hydrogen phosphate, sodium chloride, zinc salts, colloidal silica, magnesium trisilicate, polyvinyl pyrrolidone, cellulose-based substances and polyethylene glycol. Other carriers may also include sterile solutions. Compositions comprising such carriers are formulated by well known conventional methods. Such compositions may also be formulated within various lipid compositions, such as, for example, liposomes as well as in various polymeric compositions, such as polymer microspheres.

In yet another embodiment, fragments, multimers (e.g., dimers, trimers, tetramers, etc.), homologs or orthologs of PRG4 are envisioned as substitutes for PRG4. Fragments and homologs of PRG4 include those with a fewer repeats within the central mucin-like KEPAPTT-repeat domain, glycosylated and non-glycosylated forms of the protein, splice variants, recombinant forms, and the like. A lubricating fragment of PRG4 exhibits at least 20%, 30%, 40%, 50%, 60%, 70%, 80%, 90%, or 95% of the lubricating effect of human PRG4, as measured qualitatively, mechanically, optically, electrically, or by biochemical assay.

As used herein, the term "PRG4", "PRG4 protein" or "proteoglycan 4" protein, is used interchangeably with the term "lubricin" protein. PRG4 is used herein also to encompass the term megakaryocyte stimulating factor (MSF), that has been accepted for the UCL/HGNC/HUGO Human Gene Nomenclature data base, and superficial zone protein (SZP). The PRG4 or lubricin protein as used herein refers to any isolated or purified native or recombinant lubricin proteins, homologs, functional fragments or motifs, isoforms, and/or mutants thereof. In certain embodiments, the isolated or purified PRG4 protein comprises an amino acid sequence for a human native or recombinant lubricin protein. In other embodiments, the isolated or purified PRG4 protein comprises an amino acid sequence encoded by prg4gene exons that encode the full length PRG4 protein or isoforms' primary structures. The proteoglycan 4 (prg4) gene contains 12 exons. The PRG4 protein used herein comprises an amino acid sequence encoded by prg4gene exons 1-12, more preferably, exons 6-12, and most preferably, exons 9-12.

As used herein, the PRG4 protein includes any PRG4 proteins now known, or later described. In certain embodiments, a preferred PRG4 protein amino acid sequence is provided in SEQ ID NO:1. The PRG4 protein shares the primary amino acid structure of any known PRG4 proteins or isoforms with at least 60% homology, preferably 75% homology, more preferably 85%, 90%, 95%, 96%, 97%, 98%, 99% or more homology.

As used herein, the PRG4 protein comprises a biological active portion of the protein. As used herein, a "biologically active portion" of the PRG4 protein includes a fragment of a protein comprising amino acid sequences sufficiently homologous to, or derived from, the amino acid sequence of the protein, which includes fewer amino acids than the full length protein, and exhibits at least one activity of the full-length protein. Typically a biologically active portion comprises a domain or motif with at least one activity of the protein. A biologically active portion of a protein can be a polypeptide which is, for example, 10, 25, 50, 100, 200, or more amino acids in length. In one embodiment, a biologically active portion of the PRG4 protein can be used as a therapeutic agent alone or in combination with other therapeutic agents for treating undesirable or decreased ocular boundary lubrication.

The nucleic acid and amino acid sequences of several native and recombinant PRG4 or lubricin proteins, and characterization of the PRG4 proteins and various isoforms are disclosed in, for instance, U.S. Pat. Nos. 5,326,558; 6,433,142; 7,030,223; 7,361,738 to Turner et al., and U.S. Pat. Nos. 6,743,774 and 6,960,562 to Jay et al. U.S. Publication No. 20070191268 to Flannery et al. also discloses recombinant PRG4 or lubricin molecules useful in the present invention.

Methods for isolation, purification, and recombinant expression of a PRG4 protein are well known in the art. In certain embodiments, the method starts with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, and further transformed and expressed in a host cell for producing recombinant PRG4 protein.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising an active domain of the PRG4 gene and a nucleic acid sequence amplified using a primer of the invention.

In certain embodiments, the PRG4 encoding nucleic acid may contain one or more mutations, deletions, or insertions. In such embodiments, the PRG4 encoding nucleic acid is at least 60% homology, preferably 75% homology, more preferably 85%, 90%, 95%, 96%, 97%, 98%, 99%, or more homology, to a wild type PRG4 encoding nucleic acid.

As used herein, the term 'cDNAs" includes DNA that is complementary to mRNA molecules present in a cell or organism mRNA that can be convened into cDNA with an enzyme such as reverse transcriptase. In certain embodiments, the cDNA encoding PRG4 protein is isolated from PRG4 mRNA expressed in human bladder epithelial cells using an RT-PCR method well known in the art.

As used herein, the terms "polynucleotide," "nucleic acid/ nucleotide," and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, the term "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of thymine when the polynucleotide is RNA, instead of DNA. This alphabetical representation can be inputted into databases in a computer and used for bioinformatics applications such as, for example, functional genomics and homology searching.

As used herein, the term "isolated polynucleotide/cDNA" includes polynucleotide molecules which are separated from other polynucleotide molecules which are present in the natural source of the polynucleotide. For example, with regard to genomic DNA, the term "isolated" includes polynucleotide molecules which are separated from the chromosome with which the genomic DNA is naturally associated. Preferably, an "isolated" polynucleotide is free of sequences which naturally flank the polynucleotide (i.e., sequences located at the 5' and 3' ends of the polynucleotide of interest) in the genomic DNA of the organism from which the polynucleotide is derived. For example, in various embodiments, the isolated polynucleotide molecule encoding the PRG4 protein used in the invention can contain less than about 5 kb, 4 kb, 3 kb, 2 kb, 1 kb, 0.5 kb or 0.1 kb of nucleotide sequences which naturally flank the polynucleotide molecule in genomic DNA of the cell from which the polynucleotide is derived. Moreover, an "isolated" polynucleotide molecule, such as a cDNA molecule, can be substantially free of other cellular material, or culture medium when produced by recombinant techniques, or substantially free of chemical precursors or other chemicals when chemically synthesized.

As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known. As used herein, a "native or naturally-occurring" polynucleotide molecule includes, for example, an RNA or DNA molecule having a nucleotide sequence that occurs in nature (e.g., encodes a natural protein).

As used herein, the term "polypeptide" or "protein" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

In certain embodiments, the PRG4 protein used herein refers to PRG4 proteins or various homologs or isoforms thereof, that are naturally or recombinantly expressed in humans or other host cells. As used herein, "express" or "expression" includes the process by which polynucleotides are transcribed into RNA and/or translated into polypeptides. If the polynucleotide is derived from genomic DNA, expression may include splicing of the RNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general. As used herein, the term "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

As used herein, a "host cell" is intended to include any individual cell or cell culture which can be, or has been, a recipient for vectors or for the incorporation of exogenous polynucleotides and/or polypeptides. It is also intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, including but not limited to murine, rat, simian or human cells. As used herein, a "host cell" also includes genetically modified cells. The term "genetically modified cells" includes cells containing and/or expressing a foreign or exogenous gene or polynucleotide sequence which in turn modifies the genotype or phenotype of the cell or its progeny. "Genetically modified" also includes a cell containing or expressing a gene or polynucleotide sequence which has been introduced into the cell. For example, in this embodiment, a genetically modified cell has had introduced a gene which gene is also endogenous to the cell. The term "genetically modified" also includes any addition, deletion, or disruption to a cell's endogenous nucleotides. As used herein, a "host cell" can be any cells that express a human PRG4 protein.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding the PRG4 protein.

As used herein, the term "orthologs" refers to two nucleic acids from different species, but that have evolved from a common ancestral gene by speciation. Normally, orthologs encode peptides having the same or similar functions. In particular, orthologs of the invention will generally exhibit at least 80-85%, more preferably 85-90% or 90-95%, and most preferably 95%, 96%, 97%, 98%, or even 99% identity, or 100% sequence identity, with all or part of the amino acid sequence of any known PRG4 proteins, isoforms, or analogs thereof, and will exhibit a function similar to these peptides. As also used herein, the term "paralogs" refers to two nucleic acids that are related by duplication within a genome. Paralogs usually have different functions, but these functions may be related.

To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence of any known PRG4 protein.

In certain embodiments, an isolated nucleic acid homolog encoding the PRG4 protein comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences of such PRG4 protein.

The determination of the percent sequence identity between two nucleic acid or peptide sequences is well known in the art. For instance, the Vector NTI 6.0 (PC) software package (InforMax, Bethesda, Md.) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Furthermore, the PRG4 protein used herein includes PRG4 protein encoded by a polynucleotide that hybridizes to the polynucleotide encoding PRG4 protein under stringent conditions. As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under different stringent conditions. The present invention includes polynucleotides capable of hybridizing under reduced stringency conditions, more preferably stringent conditions, and most preferably highly stringent conditions, to polynucleotides encoding PRG4 protein described herein. As used herein, the term "stringent conditions" refers to hybridization overnight at 60° C. in 10×Denhart's solution, 6×SSC, 0.5% SDS, and 100 mg/ml denatured salmon sperm DNA. Blots are washed sequentially at 62° C. for 30 minutes each time in 3×SSC/0.1% SDS, followed by 1×SSC/0.1% SDS, and finally 0.1× SSC/0.1% SDS. As also used herein, in certain embodiments, the phrase "stringent conditions" refers to hybridization in a 6×SSC solution at 65° C. In other embodiments, "highly stringent conditions" refer to hybridization overnight at 65° C. in 10× Denhart's solution, 6×SSC, 0.5% SDS and 100 mg/ml denatured salmon sperm DNA. Blots are washed sequentially at 65° C. for 30 minutes each time in 3×SSC/0.1% SDS, followed by 1×SSC/0.1% SDS, and finally 0.1× SSC/0.1% SDS. Methods for nucleic acid hybridizations are well known in the art. Accordingly, the PRG4 proteins encoded by nucleic acids used herein include nucleic acid having at least 60% homology, preferably 75% homology, more preferably 85%, more preferably 90%, most preferably 95%, 96%, 97%, 98%, 99% homology to a polynucleotide sequence that encodes a human PRG4 protein or a specific isoform or homolog thereof.

Moreover, the PRG4 proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In certain embodiments of the present invention, the chimeric protein is a chimera of PRG4 protein with other PRG4 protein isoforms.

As used herein, an "isolated" or "purified" protein, polynucleotide or molecule means removed from the environment in which they naturally occur, or substantially free of cellular material, such as other contaminating proteins from the cell or tissue source from which the protein polynucleotide or molecule is derived, or substantially free from chemical precursors or other chemicals when chemically synthesized. The language "substantially free of cellular material" includes preparations separated from cellular components of the cells from which it is isolated or recombinantly produced or synthesized. In certain embodiments, the language "substantially free of cellular material" includes preparations of a PRG4 protein having less than about 30% (by dry weight) of other proteins (also referred to herein as a "contaminating protein"), more preferably less than about 20%, still more preferably less than about 10%, and most preferably less than about 5% of other proteins. When the protein or polynucleotide is recombinantly produced, it is also preferably substantially free of culture medium, i.e., culture medium represents less than about 20%, more preferably less than about 10%, and most preferably less than about 5% of the volume of the preparation of the protein of interest.

As used herein, "interstitial cystitis" and "IC" refers to a progressive disorder of the lower urinary tract that causes the symptoms of urinary frequency, urgency, and/or pelvic pain in a wide variety of patterns of presentation. An example of a recent review is Parsons, Clin Obstet Gynecol, 45(1):242-249 (2002).

As used herein, "urinary frequency" refers to the number of urination times per day.

As used herein, "urinary urgency" refers to refers to an inability to delay urination.

As used herein, "pelvic pain" refers to pain in the pelvic region of genital and non-genital origin and of organic or psychogenic aetiology.

As used herein, "urinate," "urination," "urinating," "void" and "voiding" refers to release of urine from the bladder to the outside of the body.

As used herein, "urine" refers to a liquid waste product filtered from the blood by the kidneys, stored in the bladder and expelled from the body through the urethra by the act of urinating.

As used herein, "oral," and "by oral administration" refers to the introduction of a pharmaceutical composition into a subject by way of the oral cavity (e.g. in aqueous liquid or solid form).

As used herein, "oral agent" refers to a compound that can be administered by way of the oral cavity (e.g. in aqueous liquid or solid form).

As used herein, "instill," "instilled," "instillation," refers to one or more of the following; to drop in, to pour in drop by drop, to impart gradually, to infuse slowly, to cause to be imbibed, (e.g. example infuse slowly an intravesical solution).

As used herein, "intravesical," refers to inside the bladder. As such, "intravesical instillation," "intravesical therapy," "instill," and "instillation" refers to solutions that are administered directly into the bladder. In some embodiments, instillation is via catheterization. Further, "intravesical solution," "intravesical agent," "intravesical therapeutic," and intravesical compound" refers to a treatment that can be administered to the bladder. For example, in one embodiment, an intravesical agent is intravesical heparin. In another embodiment, an intravesical agent is PPS. In one embodiment, intravesical therapy is a combination of an oral and an intravesical agent. It is not intended that the present invention be limited to a combination of an oral and an intravesical agent. For example, in one embodiment, intravesical therapy is an intravesical agent. In another embodiment, intravesical therapy is a combination of intravesical agents.

As used herein, "extravesical" refers to outside the bladder.

As used herein, "cystoscopic examination" and "cystoscopy" refers to an examination that uses a cytoscope.

As used herein, "cystoscope" refers to an endoscopic instrument to visualize the lower urinary tract, that includes the bladder and the urethra.

As used herein, "urethra" refers to a tube draining the urine to the outside. As used herein, "bladder" refers to a hollow muscular organ that stores urine until it is excreted from the body.

As used herein, the terms "subject" and "patient" refer to any animal, such as a mammal like a dog, cat, livestock, and a human (e.g. a human with a disease). In one embodiment, a patient has one or more of urinary urgency, urinary frequency, pelvic pain, recurrent urinary tract infections, dyspareunia, overactive bladder, dry, etc.).

As used herein, "urinary tract infections" refers to a condition that includes an inflamed urethra and painful urination. In some embodiments, a urinary tract infection is caused by bacteria. In some embodiments, a urinary tract infection is not caused by bacteria.

As used herein, "recurrent urinary tract infections" refers to frequent episodes of urinary tract infections.

As used herein, "overactive bladder" refers to a sudden involuntary contraction of the muscular wall of the bladder causing urinary urgency, an immediate unstoppable need to urinate and a form of urinary incontinence.

As used herein, "urinary incontinence" refers to the unintentional loss of urine and inability to control urination or prevent its leakage.

As used herein, "urinary continence" refers to a general ability to control urination.

As used herein, "catheter" refers to a tube passed through the body for draining fluids or injecting them into body cavities. It may be made of elastic, elastic web, rubber, glass, metal, or plastic.

As used herein, "catheterization" refers to the insertion of a slender tube through the urethra or through the anterior abdominal wall into the bladder, urinary reservoir, or urinary conduit to allow urine drainage.

As used herein, "catheterized" refers to the collection of a specimen by a catheterization. The terms "sample" and "specimen" are used in their broadest sense and encompass samples or specimens obtained from any source.

As used herein, the term "biological samples" refers to samples or specimens obtained from animals (including humans), and encompasses cells, fluids, solids, tissues, and gases. Biological samples include tissues (e.g., biopsy material), urine, cells, mucous, blood, and blood products such as plasma, serum and the like. However, these examples are not to be construed as limiting the types of samples which find use with the present invention.

As used herein, the term "urine cytology" refers to an examination of a urine sample that is processed in the laboratory and examined under the microscope by a pathologist who looks for the presence of abnormal cells.

As used herein, "urinary dysfunction" and "urinary tract dysfunction" refers to abnormal urination, patterns or bladder habits, including wetting, dribbling and other urination control problems.

As used herein, "heparinoid" refers to any molecule comprising a "glycosaminoglycan" which refers to a molecule comprising a network of long, branched chains of sugars (e.g. chondroitin sulphate, heparan sulphate, hyaluronic acid, keratin sulphate, dermatan sulphate, hyaluronan and the like) and optimally further comprising smaller, nitrogen-containing molecules (e.g. low molecular weight molecules). It is not meant to limit the present invention to any one glycosaminoglycan (GAG) or source of GAG. GAG molecules include but are not limited to low molecular weight (LMW) GAGS, naturally derived GAGS, biotechnologically prepared GAGS, chemically modified GAGS, synthetic GAGS, and the like. It is not meant to limit the present invention to any one heparinoid molecule or source of heparinoid molecule. As used herein, "heparin" refers to a heterogeneous group of straight-chain anionic glycosaminoglycans, as described above, having anticoagulant properties with a molecular weight ranging from 2,000 to 40,000 Da. Heparin is measured by its specific anticoagulation activity in units.

As used herein, "anesthesia" refers to a loss of feeling or inability to feel pain.

As used herein, "local anesthesia" refers to a method of pain prevention in a small area of the body.

As used herein, "low-molecular-weight heparins" refers to a lower molecular weight (LMW) species ranging from 2,000-8,000 daltons (e.g., pentosan polysulfate sodium ranging from 4,000-6,000 daltons).

As used herein, the phrases "pharmaceutically acceptable salts", "a pharmaceutically acceptable salt thereof" or "pharmaceutically accepted complex" for the purposes of this application are equivalent and refer to derivatives prepared from pharmaceutically acceptable non-toxic acids or bases including inorganic acids and bases and organic acids and bases.

As used herein, "lower urinary epithelial dysfunction" refers to disorders with positive potassium sensitivity tests (e.g. IC, prostatitis and the like).

As used herein, "urinary dysfunction" refers to abnormal urination, patterns or bladder habits, including wetting, dribbling and other urination control problems.

As used herein, "anticoagulant" refers to delaying or preventing blood coagulation. It is not meant to limit the types of sugars present on a heparin of the present invention. Five examples of sugars occurring in heparin are: (1) .alpha.-L-iduronic acid 2-sulfate, (2) 2-deoxy-2-sulfamino-a-D-glucose 6-sulfate, (3) .beta.-D-glucuronic acid, (4) 2-acetamido-2-deoxy-a-D-glucose, and (5) .alpha.-L-iduronic acid. Heparin is measured by its specific anticoagulation activity in units.

As used herein, the term "effective concentration or amount" or "therapeutically effective concentration or amount" is intended to mean a nontoxic but sufficient concentration or amount of a PRG4 protein or other therapeutic agents to provide the desired therapeutic effects. The concentration or amount that is effective will vary from subject to subject, depending on the age and general condition of the individual, the particular agents, and the like. Thus, it is not always possible to specify an exact effective concentration or amount. Furthermore, the exact effective concentration or amount of a PRG4 protein and other therapeutic agent incorporated into a composition or dosage form of the present invention is not critical, so long as the concentration is within a range sufficient to permit ready application of the solution or formulation so as to deliver an amount of the PRG4 protein and other active agents that is within a therapeutically effective range.

The pharmaceutical composition of the present invention may further comprise one or more pharmaceutically acceptable carriers or vehicles comprising any acceptable materials, and/or any one or more additives known in the art. As used herein, the term "carriers" or "vehicle" refer to carrier materials suitable for topical drug administration. Carriers and vehicles useful herein include any such materials known in the art, which are nontoxic and do not interact with other components of the composition in a deleterious manner. Various additives are optionally included in the composition. For example, solvents, including relatively small amounts of alcohol, may be used to solubilize certain drug substances. Other optional additives include opacifiers, antioxidants, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. Permeation enhancers and/or irritation-mitigating additives may also be included in the pharmaceutical composition of the present invention.

The subjects treated by the present invention include mammalian subjects, including, human, monkey, ape, dog, cat, cow, horse, goat, pig, rabbit, mouse and rat.

Throughout this application, various publications are referenced. The disclosures of all of these publications and those references cited within those publications are hereby incorporated by reference into this application for the purposes cited.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

PRG4 Formulations

A 100 µg/mL PRG4 Solution suitable for direct instillation has the following composition:

| PRG4 Solution for Instillation per mL | |
| --- | --- |
| PRG4, purified | 100 µg |
| Sodium Chloride, USP | 8.5 mg |
| Dibasic Sodium Phosphate•7H$_2$O, USP | 0.42 mg |
| Monobasic Sodium Phosphate•2H$_2$O, USP | 0.04 mg |
| Sterile Water for Injection, USP OR Sterile Water for Irrigation, USP | q.s. |

For a 20 mL dosage form, the required amount of Sodium Chloride is added (20 times the amount listed in the above table) and mixed until completely dissolved (about 15 minutes or more) in about 20 mL of water for injection or irrigation, USP. Subsequently, the required amount of monobasic and dibasic Sodium Phosphate is added to the solution. PRG4 is then added and mixed until completely dissolved. If necessary, the pH is adjusted to 7.2 with 1 N Sodium in water for injection, USP or 1 N Phosphric Acid in water for injection, USP or equivalents. A sufficient quantity to final volume with sterile water is added and mixed thoroughly.

In some embodiments, the above method is suitable for producing different unit doses of PRG4, simply by altering the volume of buffer and/or by altering the amount of PR4 and other noted components, e.g., 10-10,000 µg/mL. In further embodiments, the formulation can further comprise a preservative, e.g., benzyl alcohol or parabens (methylparaben, propylparaben, benzylparaben and mixtures thereof). In specific embodiments, the mixture is 1.5% w/v benzyl alcohol.

The above formulation is then sterile filled as 10-40 mL, e.g., 20 mL, aliquotes into 50 mL, molded Flint I type vials previously sterilized at 250° C. for 180 minutes, and stoppered using 100% synthetic rubber stoppers of the 20 mm type. The vials are then labeled as sterile PRG4 solution.

Example 2

PRG4/Heparin Sulfate Formulations

A 100 µg/mL PRG4, 100 U/mL Heparin Sulfate Solution suitable for direct instillation has the following composition:

| PRG4/Heparin Solution for Instillation per mL | |
| --- | --- |
| PRG4, purified | 100 µg |
| Heparin Sulfate, USP | 100 U |
| Sodium Chloride, USP | 8.5 mg |
| Dibasic Sodium Phosphate•7H$_2$O, USP | 0.42 mg |
| Monobasic Sodium Phosphate•2H$_2$O, USP | 0.04 mg |
| Sterile Water for Injection, USP OR Sterile Water for Irrigation, USP | q.s. |

The components in the above table are mixed in similar manners as previously described in Example 1.

Example 3

Interstitial Cystitis Pelvic Pain Murine Model and Treatment

Rationale:
PRG4 is evaluated to determine the effectiveness of reducing pseudorabies virus induced pelvic pain.

Animals:
Adult female C57BL/6J mice (10-14 weeks old) are obtained from Jackson Laboratory (Bar Harbor, Me.). Mice are housed and maintained on a regular 12:12 hour light:dark cycle with food and water ad libitum.

Induction of Neurogenic Cystitis:
Pseudorabies virus (PRV) is prepared and titrated as reported by Chen et al., J. Urol. 2006; 175(2):754-759. Neurogenic cystitis is induced by injection of $2.29 \times 10^6$ plaque-forming units of Bartha's PRV in the abductor caudalis dorsalis (ACD) muscle with a 26-gauge Hamilton syringe while maintaining the animals under isoflurane anesthesia. UV-irradiated/heat-inactivated PRV stocks are employed as negative control inocula in sham-treated mice. Both sham and PRV-infected mice are hydrated daily by subcutaneous injection of 3 ml saline in the shoulder region.

Behavioral Testing:
Mice are tested before PRV administration (baseline) and postinfection days (PID) after PRV inoculation. Referred hyperalgesia and tactile allodynia is tested using von Frey filaments applied to the abdomen and the plantar region of the hind paw. Mice are tested in individual Plexiglas chambers (6 cm×10 cm×12 cm) with a stainless steal wire grid floor (mouse acclimation period of ~10 min prior to testing). Frequency of withdrawal responses to the application of von Frey filaments to the abdomen is tested using five individual fibers with forces of 0.04, 0.16, 0.4, 1 and 4 grams (Stoelting, USA). Each filament is applied for ~1 second with an inter-stimulus interval of 2-5 s for a total 10 times, and the hairs are tested in ascending order of force. Stimulation is confined to the lower abdominal area in the general vicinity of the bladder and care is taken to stimulate different areas within this region to avoid desensitization or "wind up" effects. Three types of behaviors are considered as positive responses to filament stimulation: (1) sharp retraction of the abdomen; (2) immediate licking or scratching of the area of filament stimulation; or (3) jumping.

Therapeutic Treatment:
PRG4 therapy is administered 1 hour prior to PRV inoculation and repeated every 24 hours until PID 4. PRG4 is administered (50 µL) as a 100 µg/mL solution in distilled water and instilled into the bladder via a Hamilton syringe catheter (P10 tubing 1 cm long) while the mouse is maintained under isoflurane anesthesia. All mice are tested for referred hyperalgesia and tactile allodynia using von Frey filaments before and 45 min after treatment.

Histology:
Mice are euthanized at PID 5 and perfused with 10% neutral buffered formalin. Bladder tissues are removed and processed by fixation and section. Hematoxylin- and eosin-stained tissues are assessed by light microscopy.

Example 4

Interstitial Cystitis Bladder Inflammation Murine Model and Treatment

Rationale:
To examine the effect of PRG4 on bladder inflammation and urinary glycoasminoglycan excretion.

Animals:
Adult female Wistar rats (180 to 200 g) are obtained from Jackson Laboratory (Bar Harbor, Me.). Mice are housed and maintained on a regular 12:12 hour light:dark cycle with food and water ad libitum.

Induction of Bladder Inflammation:
Rats are anesthetized with an intraperitoneal injection of xylazine (4 mg/kg) and ketamine (90 mg/kg). External genitalia are cleansed with povidone-iodine and a small quantity of 2% lidocaine lubricant is applied to the external urethra. A 24 gauge ¾-inch catheter is inserted into the bladder and the urine is drained. Bladder injury is induced with grade X protamine sulfate (Sigma, St. Louis, Mo.), 10 mg in 200 µL sterile 0.9% saline applied intravesically. After 30 minutes, the bladder is drained and washed with 200 µL 0.9% saline. The catheter is removed and the rats are allowed to recover. Control rats are initially injected with 200 µL saline and the same procedure is followed.

Therapeutic Treatment:

To evaluate the effect of PRG4, 6 hours after protamine sulfate or saline instillation, animals are intravesically instilled with 200 µL PRG4 100 µg/mL solution in distilled water or saline each day until PID 7. Each day, animals to be sacrificed (n=5 per day) are housed 24 hours prior to sacrificed in a metabolic cage to collect urine. After sacrifice, bladders are removed and fixed in normal 10% buffered formalin and urine is immediately centrifuged to remove exfoliated cells and stored at −20° C. for further analysis.

Histopathology:

Approximately 5 µm thick paraffin sections are stained with hematoxylin and eosin for general morphology. Edema and vascular congestion are graded 0 (absent), 1 (mild), 2 (moderate) and 3 (severe). Each inflammatory cell type is counted (polymorphonuclear—PMN, mast cell and lymphomononuclear—LMN) in 5 cross sections at ×400 magnification, at the most infiltrated area.

Measurement of Urinary Hyaluronic Acid and Suflated Glycoasminoglycans (GAGs):

Urinary hyaluronic acid (HA) levels are measured by a noncompetitive and nonisotopic fluoroassay. Plates are coated with hyaluronan binding proteins (HABP) and successively incubated with samples containing standard solutions of HA or urine samples from the different groups, biotin-conjugated HABP and europium-labeled streptavidin (Amersham Life Science, Buckinghamshire, England). After release of europium from streptavidin with enhancement solution (Perkin-Elmer Life Sciences-Wallac Oy, Turku, Finland) the final fluorescence is measured in a fluorometer. HA levels are then normalized to creatinine concentrations.

For urinary sulfated GAGs, 2 mL of urine are applied to a gel filtration column of the G25 type available under the brand name SEPHADEX from GE Healthcare Bio-Sciences AB, Private Limited Liability Company, Sweden, 30 Bjorkgagtan, Uppsala, SWEDEN SE-75184, equilibrated with distilled water. The inclusion volume is discarded and the following 4 mL flow-through is collected, vacuum dried and then dissolved in 10 mµL distilled water and kept frozen for at −20.degree. C. analysis. 5 mµL of the stored samples and 5 mµL of an aqueous standard of 1 mg/mL GAG (Chondroitin 4- and 6-sulfate, dermatan sulfate and heparan sulfate) are applied to 0.2-cm thick agarose gel slabs (0.55% agarose in 50 nM 1,3-aminopropane/acetate buffer, pH 9.0) to proceed with electrophoresis. Gel slabs are fixed with 0.1% cetyltrimethyl-ammonium bromide, dried, stained with toluidine blue and quantified by densitometry at 595 nm. GCG concentration is normalized to creatinine concentrations.

Example 5

Pilot Clinical Investigation of the Efficacy and Safety of PRG4 Versus Placebo in Patients With Interstitial Cystitis/Painful Bladder Syndrome Purpose:

A pilot clinical investigation regarding the safety and efficacy of PRG4 formulation of Example 1 versus a vehicle placebo in patients with interstitial cystitis/painful bladder syndrome (IC/PBS)

Inclusion Criteria:

Female or Male patients 18 years or older; have been previously diagnosed with IC/PBS; are willing to provide informed consent; and available for duration of study including treatment and follow-up (12 weeks)

Exclusion Criteria:

Pregnant or lactating female; are currently or previously received investigational drugs within 30 days of screening; previous therapy for IC/PBS; have any medical condition/disease that could interfere with patient compliance or interfere with interpretation of study; unable to read understand or provide written informed consent Treatment Arms:

| Arms | Assigned Interventions |
| --- | --- |
| Experimental PRG4 solution (Example 1) | 20 mL for weekly intravesical instillation for 6 consecutive weeks |
| Placebo: Placebo Comparator | Placebo bladder instillation weekly for 6 consecutive weeks |

Primary Outcome Measures:

Subjective improvement assessed by several questionnaires: Oleary Sant symptom index score, bladder diary, 1-10 visual analogue scale for pain, PSQ4 questionnaire.

Objective improvement assessed by urodynamic test including cystometric capacity, $1^{st}$ sensation & normal sensation.

Secondary Outcome Measures:

Adverse event assessments from first instillation to Week 12.

Other features and advantages of the invention will be apparent from the following description of the preferred embodiments thereof and from the claims.

SEQUENCE LIST

SEQ ID NO: 1

MAWKTLPIYLLLLLSVFVIQQVSSQDLSSCAGRCGEGYSRDATCNCDYNC

QHYMECCPDFKRVCTAELSCKGRCFESFERGRECDCDAQCKKYDKCCPDY

ESFCAEVHNPTSPPSSKKAPPPSGASQTIKSTTKRSPKPPNKKKTKKVIE

SEEITEEHSVSENQESSSSSSSSSSSSSTIRKIKSSKNSAANRELQKKLKV

KDNKKNRTKKKPTPKPPVVDEAGSGLDNGDFKVTTPDTSTTQHNKVSTSP

KITTAKPINPRPSLPPNSDTSKETSLTVNKETTVETKETTTTNKQTSTDG

KEKTTSAKETQSIEKTSAKDLAPTSKVLAKPTPKAETTTKGPALTTPKEP

TPTTPKEPASTTPKEPTPTTIKSAPTTPKEPAPTTTKSAPTTPKEPAPTT

TKEPAPTTPKEPAPTTTKEPAPTTTKSAPTTPKEPAPTTPKKPAPTTPKE

PAPTTPKEPTPTTPKEPAPTTKEPAPTTPKEPAPTAPKKPAPTTPKEPAP

TTPKEPAPTTTKEPSPTTPKEPAPTTTKSAPTTTKEPAPTTTKSAPTTPK

EPSPTTTKEPAPTTPKEPAPTTPKKPAPTTPKEPAPTTPKEPAPTTTKKP

APTTPKEPAPTTPKETAPTTPKKLTPTTPEKLAPTTPEKPAPTTPEELAP

TTPEEPTPTTPEEPAPTTPKAAAPNTPKEPAPTTPKEPAPTTPKEPAPTT

PKETAPTTPKGTAPTTLKEPAPTTPKKPAPKELAPTTTKEPTSTTCDKPA

PTTPKGTAPTTPKEPAPTTPKEPAPTTPKGTAPTTLKEPAPTTPKKPAPK

ELAPTTTKGPTSTTSDKPAPTTTPKETAPTTPKEPAPTTPKKPAPTTPETP

```
PPTTSEVSTPTTTKEPTTIHKSPDESTPELSAEPTPKALENSPKEPGVPT
TKTPAATKPEMTTTAKDKTTERDLRTTPETTTAAPKMTKETATTTEKTTE
SKITATTTQVTSTTTQDTTPFKITTLKTTTLAPKVTTTKKTITTTEIMNK
PEETAKPKDRATNSKATTPKPQKPTKAPKKPTSTKKPKTMPRVRKPKTTP
TPRKMTSTMPELNPTSRIAEAMLQTTTRPNQTPNSKLVEVNPKSEDAGGA
EGETPHMLLRPHVFMPEVTPDMDYLPRVPNQGIIINPMLSDETNICNGKP
VDGLTTLRNGTLVAFRGHYFWMLSPFSPPSPARRITEVWGIPSPIDTVFT
RCNCEGKTFFFKDSQYWRFTNDIKDAGYPKPIFKGFGGLTGQIVAALSTA
```

```
KYKNWPESVYFFKRGGSIQQYIYKQEPVQKCPGRRPALNYPVYGETTQVR
RRRFERAIGPSQTHTIRIQYSPARLAYQDKGVLHNEVKVSILWRGLPNVV
TSAISLPNIRKPDGYDYYAFSKDQYYNIDVPSRTARAITTRSGQTLSKVW
YNCP
```

SEQ ID NO: 2:
GATGCAGGGTACCCCAAA (human, sense)

SEQ ID NO: 3:
CAGACTTTGGATAAGGTCTGCC (human, antisense)

---

What is claimed is:

1. A method for treating interstitial cystitis or symptoms associated therewith in a subject in need thereof, comprising administering a therapeutically effective amount of a pharmaceutical composition comprising proteoglycan 4 (PRG4), wherein the wherein the PRG4 comprises an interstitial cystitis reducing amount of the full-length protein of SEQ ID NO: 1.

2. The method of claim 1, wherein the PRG4 is a purified or a recombinant form of PRG4.

3. The method of claim 1, wherein the PRG4 has an average molar mass of between 50 kDa and 400 kDa.

4. The method of claim 1, wherein the PRG4 is in a therapeutically effective concentration of between 10-10,000 μg/mL or 50-500 μg/mL.

5. The method of claim 1, further comprising administering a therapeutically effective amount of an osmolar component.

6. The method of claim 5, wherein the composition is in solution and the osmolar component is in a sufficient amount so that the final solution is isotonic or near isotonic.

7. The method of claim 5, wherein the osmolar component is at least one of sodium chloride, dextrose, dextran 40, dextran 60, starch, and mannitol.

8. The method of claim 1, further comprising administering a therapeutically effective amount of a local anesthetic agent.

9. The method of claim 8, wherein the local anesthetic agent is at least one of lidocaine, bupivacaine, and mepivacaine.

10. The method of claim 8, wherein the effective amount of the anesthetic agent is 10 ml of 1% lidocaine or 16 ml of 2% lidocaine per unit dose.

11. The method of claim 1, further comprising administering a therapeutically effective amount of a heparinoid.

12. The method of claim 11, wherein the heparinoid is at least one of a heparin, a pentosan polysulfate sodium, a heparan sulfate, a heparin sodium, a hyaluronic acid and a chondroitin sulfate.

13. The method of claim 12, wherein the effective amount of the heparinoid is between (i) about 0.5 mg to about 1000 mg of heparin per unit dose; (ii) about 1 mg to about 600 mg of pentosan polysulfate sodium per unit dose; (iii) about 0.5 mg to about 10,000 mg of heparan sulfate per unit dose; (iv) about 1 mg to about 600 mg of hyaluronic acid per unit dose; (v) about 1 mg to about 10,000 mg of chondroitin sulfate per unit dose; or (vi) about 10 mg to about 600 mg of heparin sodium per unit dose.

14. The method of claim 1, further comprising administering a therapeutically effective amount of sodium pentosan polysulfate.

15. The method of claim 14, wherein the sodium pentosan polysulfate is in an amount from about 100 mg/day to about 600 mg/day or about 100 mg/day to about 300 mg/day.

16. The method of claim 1, further comprising administering a surface active phospholipid.

17. The method of claim 16, wherein the surface active phospholipid is selected from the group consisting of L-a-dipalmitoylphosphatidylcholine, phosphatidylcholine, phosphatidylethanolamine and sphingomyelin.

18. The method of claim 16, wherein the surface active phospholipid is in a therapeutically effective concentration between 10-10,000 μg/mL.

19. The method of claim 1, further comprising administering a PRG4 inducing compound, comprising at least one of an androgen, an androgen analogue, a selective androgen receptor modulator, a selective estrogen receptor modulator, an estrogen antagonist, an aromatase inhibitor, an antiprotease, a proinflammatory cytokine antagonist, a cytokine release inhibitor, an antiinflammatory cytokine, an antiinflammatory agent, a NF-k-B inhibitor, and a proteasome inhibitor.

20. The method of claim 1, wherein the composition is administered intravesicularly, intramuscularly, intravenously, using liposomes, using biodegradable polymers, using a hydrogel, or by direct instillation into the bladder.

21. A method for repairing a mucin layer of bladder tissue in a subject in need thereof, comprising administering a therapeutically effective amount of a pharmaceutical composition comprising PRG4, wherein the PRG4 comprises the full-length protein of SEQ ID NO: 1.

* * * * *

SEQUENCE LISTING

<160> NUMBER OF SEQ ID NOS: 3

<210> SEQ ID NO 1
<211> LENGTH: 1404
<212> TYPE: PRT
<213> ORGANISM: Homo sapiens

<400> SEQUENCE: 1

Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
                20                  25                  30

Arg Cys Gly Glu Gly Tyr Ser Arg Asp Ala Thr Cys Asn Cys Asp Tyr
            35                  40                  45

Asn Cys Gln His Tyr Met Glu Cys Cys Pro Asp Phe Lys Arg Val Cys
        50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Pro Asn Lys Lys Lys
        130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Asn Arg Thr
        195                 200                 205

Lys Lys Lys Pro Thr Pro Lys Pro Pro Val Val Asp Glu Ala Gly Ser
210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Asn Ser Asp Thr Ser Lys
            260                 265                 270

-continued

```
Glu Thr Ser Leu Thr Val Asn Lys Glu Thr Thr Val Glu Thr Lys Glu
            275                 280                 285
Thr Thr Thr Thr Asn Lys Gln Thr Ser Thr Asp Gly Lys Glu Lys Thr
        290                 295                 300
Thr Ser Ala Lys Glu Thr Gln Ser Ile Glu Lys Thr Ser Ala Lys Asp
305                 310                 315                 320
Leu Ala Pro Thr Ser Lys Val Leu Ala Lys Pro Thr Pro Lys Ala Glu
                325                 330                 335
Thr Thr Thr Lys Gly Pro Ala Leu Thr Thr Pro Lys Glu Pro Thr Pro
            340                 345                 350
Thr Thr Pro Lys Glu Pro Ala Ser Thr Thr Pro Lys Glu Pro Thr Pro
        355                 360                 365
Thr Thr Ile Lys Ser Ala Pro Thr Thr Pro Lys Glu Pro Ala Pro Thr
    370                 375                 380
Thr Thr Lys Ser Ala Pro Thr Thr Pro Lys Glu Pro Ala Pro Thr Thr
385                 390                 395                 400
Thr Lys Glu Pro Ala Pro Thr Thr Pro Lys Glu Pro Ala Pro Thr Thr
                405                 410                 415
Thr Lys Glu Pro Ala Pro Thr Thr Lys Ser Ala Pro Thr Thr Pro
            420                 425                 430
Lys Glu Pro Ala Pro Thr Thr Pro Lys Lys Pro Ala Pro Thr Thr Pro
        435                 440                 445
Lys Glu Pro Ala Pro Thr Thr Pro Lys Glu Pro Thr Pro Thr Thr Pro
    450                 455                 460
Lys Glu Pro Ala Pro Thr Thr Lys Glu Pro Ala Pro Thr Thr Pro Lys
465                 470                 475                 480
Glu Pro Ala Pro Thr Ala Pro Lys Lys Pro Ala Pro Thr Thr Pro Lys
                485                 490                 495
Glu Pro Ala Pro Thr Thr Pro Lys Glu Pro Ala Pro Thr Thr Thr Lys
            500                 505                 510
Glu Pro Ser Pro Thr Thr Pro Lys Glu Pro Ala Pro Thr Thr Thr Lys
        515                 520                 525
Ser Ala Pro Thr Thr Lys Glu Pro Ala Pro Thr Thr Lys Ser
    530                 535                 540
Ala Pro Thr Thr Pro Lys Glu Pro Ser Pro Thr Thr Lys Glu Pro
545                 550                 555                 560
Ala Pro Thr Thr Pro Lys Glu Pro Ala Pro Thr Pro Lys Lys Pro
                565                 570                 575
Ala Pro Thr Thr Pro Lys Glu Pro Ala Pro Thr Pro Lys Glu Pro
            580                 585                 590
Ala Pro Thr Thr Lys Lys Pro Ala Pro Thr Thr Pro Lys Glu Pro
        595                 600                 605
Ala Pro Thr Thr Pro Lys Glu Thr Ala Pro Thr Pro Lys Lys Leu
    610                 615                 620
Thr Pro Thr Thr Pro Glu Lys Leu Ala Pro Thr Thr Pro Glu Lys Pro
625                 630                 635                 640
Ala Pro Thr Thr Pro Glu Glu Leu Ala Pro Thr Thr Pro Glu Glu Pro
                645                 650                 655
Thr Pro Thr Thr Pro Glu Glu Pro Ala Pro Thr Thr Pro Lys Ala Ala
            660                 665                 670
Ala Pro Asn Thr Pro Lys Glu Pro Ala Pro Thr Thr Pro Lys Glu Pro
        675                 680                 685
```

```
Ala Pro Thr Thr Pro Lys Glu Pro Ala Pro Thr Thr Pro Lys Glu Thr
690                 695                 700
Ala Pro Thr Thr Pro Lys Gly Thr Ala Pro Thr Thr Leu Lys Glu Pro
705                 710                 715                 720
Ala Pro Thr Thr Pro Lys Lys Pro Ala Pro Lys Glu Leu Ala Pro Thr
                725                 730                 735
Thr Thr Lys Glu Pro Thr Ser Thr Thr Cys Asp Lys Pro Ala Pro Thr
            740                 745                 750
Thr Pro Lys Gly Thr Ala Pro Thr Thr Pro Lys Glu Pro Ala Pro Thr
            755                 760                 765
Thr Pro Lys Glu Pro Ala Pro Thr Thr Pro Lys Gly Thr Ala Pro Thr
        770                 775                 780
Thr Leu Lys Glu Pro Ala Pro Thr Thr Pro Lys Lys Pro Ala Pro Lys
785                 790                 795                 800
Glu Leu Ala Pro Thr Thr Thr Lys Gly Pro Thr Ser Thr Thr Ser Asp
                805                 810                 815
Lys Pro Ala Pro Thr Thr Pro Lys Glu Thr Ala Pro Thr Thr Pro Lys
            820                 825                 830
Glu Pro Ala Pro Thr Thr Pro Lys Lys Pro Ala Pro Thr Thr Pro Glu
        835                 840                 845
Thr Pro Pro Thr Thr Ser Glu Val Ser Thr Pro Thr Thr Thr Lys
850                 855                 860
Glu Pro Thr Thr Ile His Lys Ser Pro Asp Glu Ser Thr Pro Glu Leu
865                 870                 875                 880
Ser Ala Glu Pro Thr Pro Lys Ala Leu Glu Asn Ser Pro Lys Glu Pro
                885                 890                 895
Gly Val Pro Thr Thr Lys Thr Pro Ala Ala Thr Lys Pro Glu Met Thr
            900                 905                 910
Thr Thr Ala Lys Asp Lys Thr Thr Glu Arg Asp Leu Arg Thr Thr Pro
        915                 920                 925
Glu Thr Thr Thr Ala Ala Pro Lys Met Thr Lys Glu Thr Ala Thr Thr
930                 935                 940
Thr Glu Lys Thr Thr Glu Ser Lys Ile Thr Ala Thr Thr Thr Gln Val
945                 950                 955                 960
Thr Ser Thr Thr Thr Gln Asp Thr Thr Pro Phe Lys Ile Thr Thr Leu
            965                 970                 975
Lys Thr Thr Thr Leu Ala Pro Lys Val Thr Thr Thr Lys Lys Thr Ile
            980                 985                 990
Thr Thr Thr Glu Ile Met Asn Lys Pro Glu Glu Thr Ala Lys Pro Lys
        995                 1000                1005
Asp Arg Ala Thr Asn Ser Lys Ala Thr Thr Pro Lys Pro Gln Lys
    1010                1015                1020
Pro Thr Lys Ala Pro Lys Lys Pro Thr Ser Thr Lys Lys Pro Lys
    1025                1030                1035
Thr Met Pro Arg Val Arg Lys Pro Lys Thr Pro Thr Pro Arg
    1040                1045                1050
Lys Met Thr Ser Thr Met Pro Glu Leu Asn Pro Thr Ser Arg Ile
    1055                1060                1065
Ala Glu Ala Met Leu Gln Thr Thr Thr Arg Pro Asn Gln Thr Pro
    1070                1075                1080
Asn Ser Lys Leu Val Glu Val Asn Pro Lys Ser Glu Asp Ala Gly
    1085                1090                1095
Gly Ala Glu Gly Glu Thr Pro His Met Leu Leu Arg Pro His Val
```

```
                  1100                1105                1110

Phe Met Pro Glu Val Thr Pro Asp Met Asp Tyr Leu Pro Arg Val
            1115                1120                1125

Pro Asn Gln Gly Ile Ile Ile Asn Pro Met Leu Ser Asp Glu Thr
            1130                1135                1140

Asn Ile Cys Asn Gly Lys Pro Val Asp Gly Leu Thr Thr Leu Arg
            1145                1150                1155

Asn Gly Thr Leu Val Ala Phe Arg Gly His Tyr Phe Trp Met Leu
            1160                1165                1170

Ser Pro Phe Ser Pro Pro Ser Pro Ala Arg Arg Ile Thr Glu Val
            1175                1180                1185

Trp Gly Ile Pro Ser Pro Ile Asp Thr Val Phe Thr Arg Cys Asn
            1190                1195                1200

Cys Glu Gly Lys Thr Phe Phe Phe Lys Asp Ser Gln Tyr Trp Arg
            1205                1210                1215

Phe Thr Asn Asp Ile Lys Asp Ala Gly Tyr Pro Lys Pro Ile Phe
            1220                1225                1230

Lys Gly Phe Gly Gly Leu Thr Gly Gln Ile Val Ala Ala Leu Ser
            1235                1240                1245

Thr Ala Lys Tyr Lys Asn Trp Pro Glu Ser Val Tyr Phe Phe Lys
            1250                1255                1260

Arg Gly Gly Ser Ile Gln Gln Tyr Ile Tyr Lys Gln Glu Pro Val
            1265                1270                1275

Gln Lys Cys Pro Gly Arg Arg Pro Ala Leu Asn Tyr Pro Val Tyr
            1280                1285                1290

Gly Glu Thr Thr Gln Val Arg Arg Arg Phe Glu Arg Ala Ile
            1295                1300                1305

Gly Pro Ser Gln Thr His Thr Ile Arg Ile Gln Tyr Ser Pro Ala
            1310                1315                1320

Arg Leu Ala Tyr Gln Asp Lys Gly Val Leu His Asn Glu Val Lys
            1325                1330                1335

Val Ser Ile Leu Trp Arg Gly Leu Pro Asn Val Val Thr Ser Ala
            1340                1345                1350

Ile Ser Leu Pro Asn Ile Arg Lys Pro Asp Gly Tyr Asp Tyr Tyr
            1355                1360                1365

Ala Phe Ser Lys Asp Gln Tyr Tyr Asn Ile Asp Val Pro Ser Arg
            1370                1375                1380

Thr Ala Arg Ala Ile Thr Thr Arg Ser Gly Gln Thr Leu Ser Lys
            1385                1390                1395

Val Trp Tyr Asn Cys Pro
            1400

<210> SEQ ID NO 2
<211> LENGTH: 18
<212> TYPE: DNA
<213> ORGANISM: Homo sapiens

<400> SEQUENCE: 2
gatgcagggt accccaaa                                                 18

<210> SEQ ID NO 3
<211> LENGTH: 22
<212> TYPE: DNA
<213> ORGANISM: Homo sapiens
```

```
<400> SEQUENCE: 3
cagactttgg ataaggtctg cc                                              22
```